United States Patent [19]

Chen

[11] Patent Number: 5,122,963
[45] Date of Patent: Jun. 16, 1992

[54] ACTUATION CELL RESPONSE AND MAPPING DETERMINATIONS FOR WEB FORMING MACHINES

[75] Inventor: Shih-Chin Chen, Dublin, Ohio

[73] Assignee: Process Automation Business, Inc., Columbus, Ohio

[21] Appl. No.: 489,497

[22] Filed: Mar. 7, 1990

[51] Int. Cl.$^5$ .................... G06F 15/46; G05B 13/02
[52] U.S. Cl. .................... 364/471; 364/158; 364/473; 364/469; 73/159
[58] Field of Search ............ 364/158, 159, 468, 469, 364/471, 473, 551.01, 552, 553, 554, 178; 73/159

[56] References Cited

U.S. PATENT DOCUMENTS

| | | | |
|---|---|---|---|
| 4,451,878 | 5/1984 | Shigemusa | 364/159 |
| 4,707,779 | 11/1987 | Hu | 364/471 |
| 4,855,658 | 8/1989 | Moon | 364/469 |
| 4,882,526 | 11/1989 | Iino et al. | 364/158 |
| 4,939,929 | 7/1990 | Ostman | 364/471 |
| 4,947,684 | 8/1990 | Balakrishnan | 364/471 |

OTHER PUBLICATIONS

S.-C. Chen, R. M. Snyder, R. G. Wilhelm, Jr., "Adaptive Profile Control for Sheetmaking Processes", Oct. 1986.
A. Graser, W. Neddermeyer, "Self-Tuning Cross Profile for a Paper Machine", Istanbul, Turkey 1986.

Primary Examiner—Jerry Smith
Assistant Examiner—Jim Trummell
Attorney, Agent, or Firm—Killworth, Gottman, Hagan & Schaeff

[57] ABSTRACT

A standard control signal for a web forming machine is temporarily interrupted and replaced by a perturbing signal or signgals which are applied to one, a grouping, or all of a series of actuation cells of the web forming machine. One or more actuation cells are driven with an alternating perturbing signal(s) which generate a corresponding action in the actuation cell(s). The perturbing signal(s) alternates from a neutral position of the cell and is selected to minimize means effects over any given period of time. The effects of the alternating signal(s) on the web appear within the area of the web which is affected by the actuation cell(s) such that the mapping and the response of the actuation cell(s) can be determined by monitoring that poriton of the web which is formed while the alternating signal(s) is applied to the actuation cell(s). The mapping(s) and/or response(s) of the actuation cell(s) are obtained by correlating the perturbing signal(s) and a web property signal or profile signal obtained by monitoring the web formed by the machine. The perturbing signal(s) is defined by a pseudo-random binary sequence with multiple signals being selected to be statistically independent of one another. To ensure that the web is not perturbed beyond defined specifications, the perturbing signal preferably is gradually increased in amplitude and is terminated individually for each actuation cell upon reaching a usable amplitude.

21 Claims, 7 Drawing Sheets

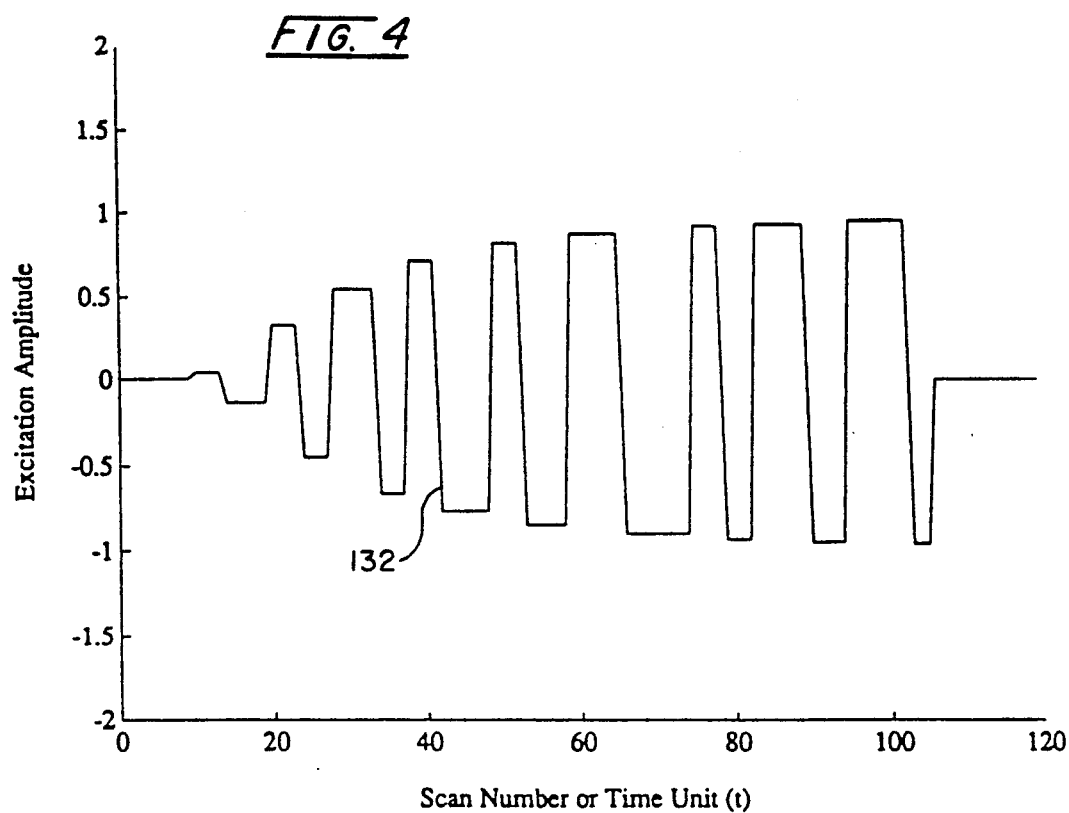
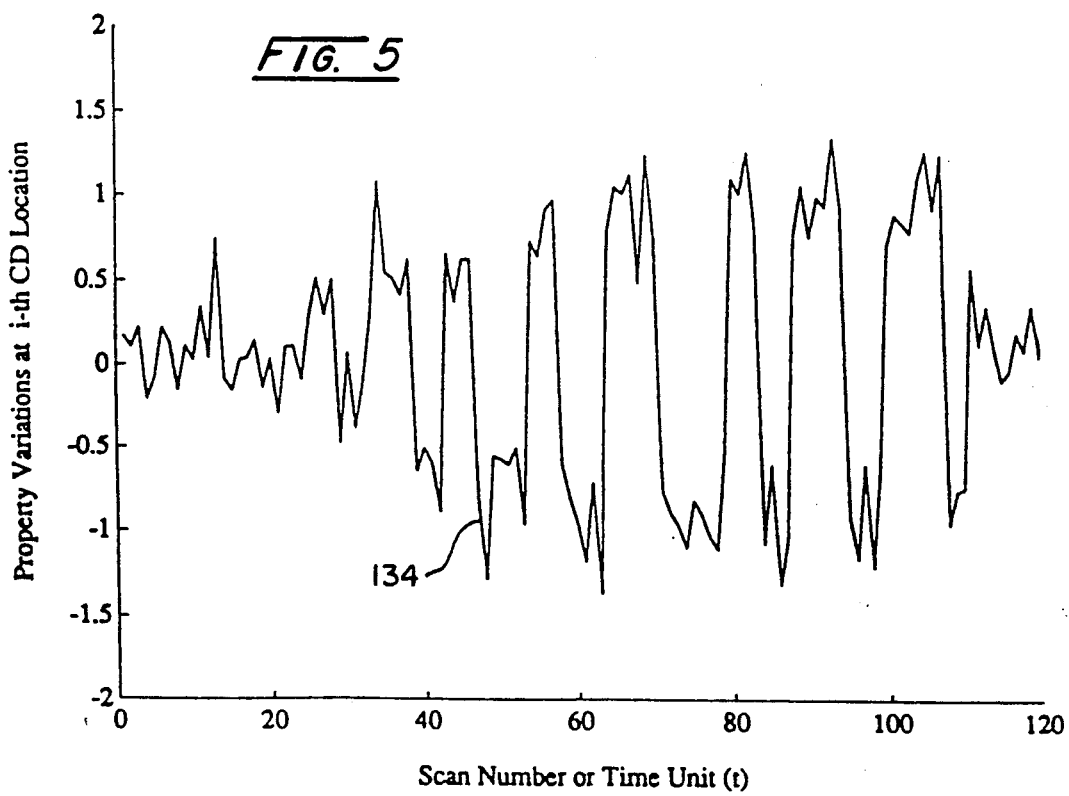

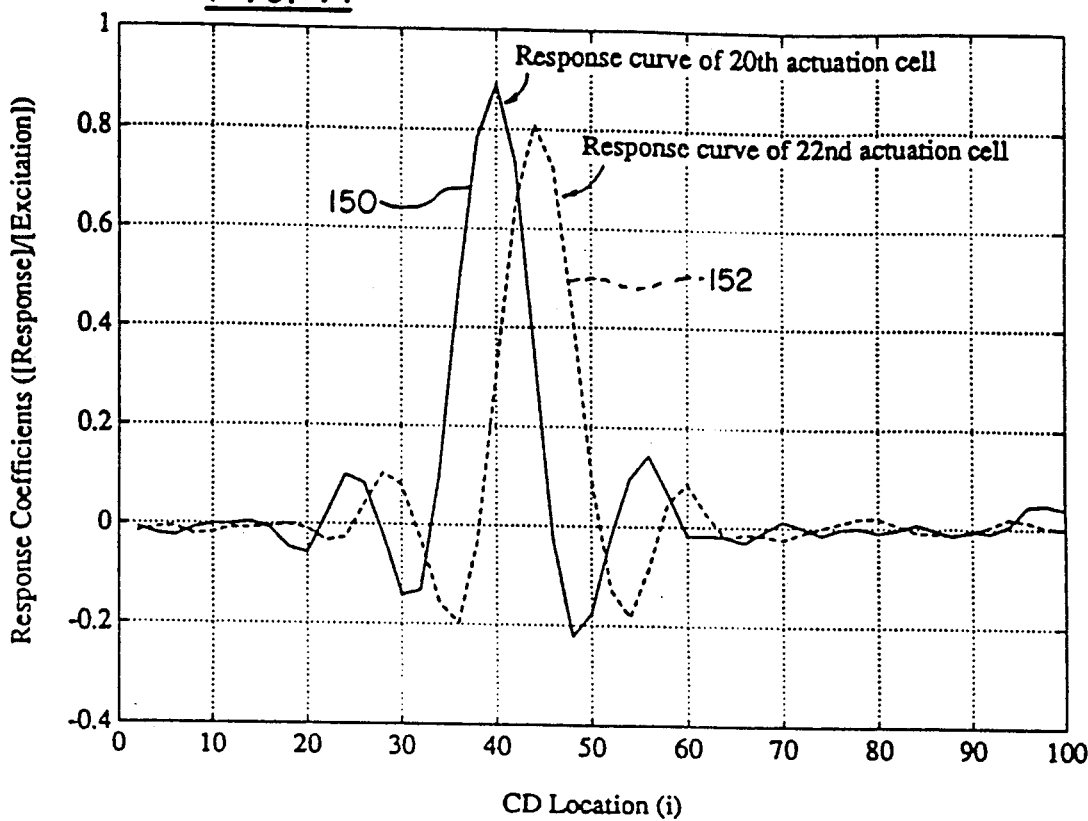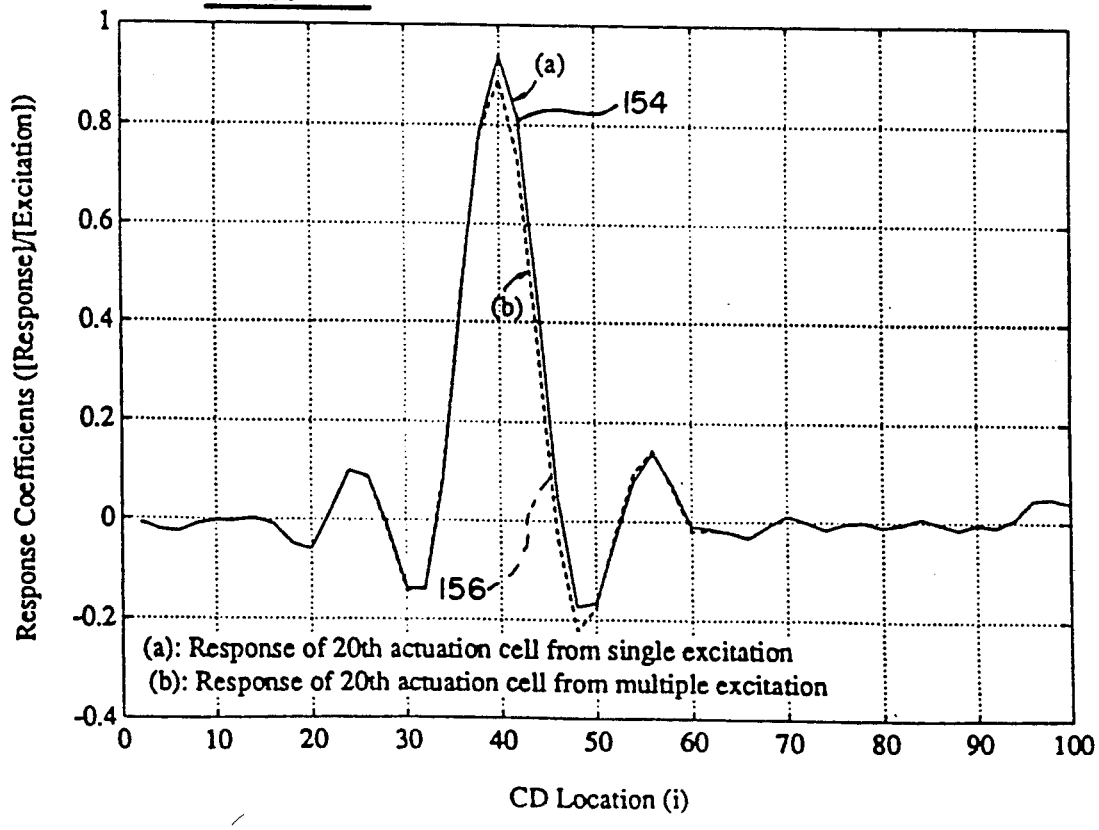

ACTUATION CELL RESPONSE AND MAPPING DETERMINATIONS FOR WEB FORMING MACHINES

BACKGROUND OF THE INVENTION

The present invention relates generally to machines for forming webs of sheet material and, more particularly, to a method and apparatus for determining cross direction responses and mappings of actuation cells used to control the operation of such machines.

Machines which produce webs of sheet material such as paper, plastic and aluminum, face common process control problems in producing webs which satisfy specifications for the given sheet material. Web specifications commonly include ranges for characteristics of the web including thickness, moisture content, weight per unit area and the like. Quality control is complicated since the specified characteristics vary in both the machine direction (MD) or direction of movement of the web through the machine and in the machine cross direction (CD) or laterally across the web.

The MD variations are generally affected by factors that impact the entire width of the web, such as machine speed, the source of base material being formed into a web by the machine, common supplies of working fluids like steam, and similar factors. CD variations, represented by profiles or profile signals, are normally controlled by arrays of actuation cells distributed across the width of the machine. On paper making machines, for which the present invention is particularly applicable, the CD actuation cells include basis weight actuators which control the slice of a headbox, steam shower nozzles, infrared (IR) heaters which control CD moisture variations, and other known devices.

Adjustment of CD actuation cells generally affects a portion of the profile that is wider than the individual actuation cells. Thus, for controlling the CD profile of a web forming machine, it is important to know which portion of the profile is affected by each CD actuation cell and how the profile is changed by adjustments of each CD actuation cell. The functional relationship that describes which part of the profile is affected by each CD actuation cell is called "mapping" of the CD actuator cells. The functional curve that indicates how the process profile is changed by the adjustment of a CD actuation cell is called the "response" of the CD actuation cell.

Not only does the CD response of an actuator cell typically spread over a much wider area than the area of the cell itself, but also the CD mapping of an actuator cell can vary or shift for different operating conditions. To obtain a desired profile for the web of sheet material being formed, it is essential to have response and mapping information which precisely corresponds to each actuation cell and also to the different operating conditions which the cell may encounter.

In the past, response information typically has been determined on-line by means of feedback arrangements. In these systems, the control signals which are passed to the machine to maintain the web forming process within suitable limits are monitored and compared to a profile signal which is generated by monitoring the web of material within the machine or as it emerges from the machine. Unfortunately, since the control signals must be substantially limited in terms of amplitude excursions, the resulting response and mapping characteristics are not as representative as is desired for accurate control of the machine.

Another system has been described for determining both response and mapping information by interrupting a system controller and then changing the setting of a given actuation cell. The actuation cell is changed a number of times and the resulting changes in the web are monitored. By summing and otherwise processing these changes, the response and mapping for the actuation cell can be determined. Unfortunately, the described system requires a substantial period of time to evaluate one or more series of actuation cells. Further, there is no assurance that the web being produced during the evaluation will be within required specification limits such that the web can be used.

Accordingly, there is a need for improved determination of the response and mapping characteristics of the individual actuation cells of web forming machines. The response and mapping characteristics should be quickly and accurately obtained, even while the machine is operating and without adversely affecting the quality of the web of material being formed. Preferably, any method and/or apparatus for determining the response and mapping characteristics could be inexpensively incorporated into new machines and also retrofitted into existing machines with substantially equal improvements in the operations of the existing machines.

SUMMARY OF THE INVENTION

This need is met by the method and apparatus of the present invention wherein a standard control signal for a web forming machine is temporarily interrupted and replaced by a perturbing signal which is applied to one, a grouping, or all of a series of actuation cells of the web forming machine. In its most basic implementation, an actuation cell is driven with an alternating perturbing signal which generates a corresponding action in the actuation cell. The signal alternates from a neutral position of the cell and is selected to minimize mean effects over any given period of time. The effects of the alternating signal on the web appear within that area of the web which is affected by the actuation cell such that the mapping and the response of the actuation cell can be determined by monitoring that portion of the web which is formed while the alternating signal is applied to the actuation cell. In the present invention, the mapping and/or response of the actuation cell are obtained by correlating the perturbing signal and a web property signal or profile signal obtained by monitoring the web formed by the machine.

To speed up the determination of the mapping and response of all the actuation cells of a web forming machine, perturbing signals can be applied to groups of actuation cells, with cells within each group being spaced from one another by a sufficient distance to substantially prevent interference between or among perturbing signals. The resulting mappings and responses can be interpolated or additional groups can be stimulated to arrive at mappings and responses for all the actuation cells.

To further speed up the determination, all of the actuation cells can be driven simultaneously with the resulting web effects being monitored and separated to determine the mappings and responses of all of the actuation cells. For simultaneous excitation of all actuation cells, each cell is driven with a particular sequence of alternating signals which is unique for that cell and hence can be recognized in the resulting perturbations of the portion of the web which is formed while the signals are being applied. Recognition of the perturbations due to individual actuation cells is possible even though the perturbations of adjacent cells overlap one another and visually appear inseparable, since the activation signals are selected to be substantially independent of one another.

To this end, activation signals are preferably defined by pseudo-random binary sequences which are selected to be statistically independent of one another. To simplify selection of independent sequences, it has been recognized that a pool of independent sequences may be repeated in groupings across the machine, provided the groupings are of sufficient size that each signal in one group is separated from the same signal in an adjacent group such that there is substantially no interference between the two. To ensure that the web is not perturbed beyond defined specifications for the web, the perturbing signal preferably is gradually increased in amplitude. The perturbing signal amplitude is increased until its result is sufficiently recognizable in the web to satisfactorily determine the mappings and responses of the actuation cells of the web forming machine but not to the point of exceeding specification limits.

In accordance with one aspect of the present invention, a method for determining the cross direction responses and mappings of actuation cells extending across the width of a machine used for manufacturing a web of sheet material comprises the steps of: applying a perturbing signal to at least one actuation cell, the perturbing signal alternating about a neutral state of the actuation cell to minimize mean effects over any given time period of signal application; measuring a property of the web of sheet material produced by the machine during application of the perturbing signal to generate a corresponding web property signal; and, correlating the perturbing signal and the web property signal to determine the cross direction response and mapping of the at least one actuation cell for the property.

In accordance with another aspect of the present invention, a method for determining the cross direction responses and mappings of actuation cells extending across the width of a machine used for manufacturing a web of sheet material comprises the steps of: applying perturbing signals to a plurality of the actuation cells, the perturbing signals alternating about a neutral state of the actuation cells to minimize mean effects over any given time period of signal application; measuring a property of the web of sheet material produced by the machine during application of the perturbing signals to generate a corresponding web property signal; and, correlating the perturbing signals and the web property signal to determine the cross direction responses and mappings of the plurality of actuation cells for the property.

The method may further comprise the step of modulating the perturbing signal such that its amplitude is gradually increased from a low level to a level at which web property perturbations resulting from the perturbing signal are distinguishable from noise perturbations encountered during normal machine operation, but web specifications are not compromised. The durations of alternations of each perturbing signal preferably are randomly distributed between defined limits to ensure detection of resulting perturbations. The step of applying a perturbing signal may comprise applying a perturbing signal to a plurality of actuation cells which are spaced apart from one another by a distance such that perturbations generated by the application of the perturbing signal to any one of the plurality of actuation cells does not substantially affect perturbations generated by the application of the perturbing signal to any other one of the plurality of actuation cells.

To fully define the response of the actuation cells, the method further comprises the step of determining the center of the response for the actuation cells. To substantially prevent interference between closely positioned actuation cells, the perturbing signals may comprise a plurality of substantially independent excitation patterns. Preferably, the perturbing signals comprise a plurality of statistically independent pseudo-random binary sequences, particularly where perturbing signals are applied to all of the actuation cells. To reduce the number of such sequences which are required for a given machine, the perturbing signals can be applied in groups of repetitively occurring statistically independent pseudo-random binary sequences, the groups being of sufficient size such that recurring perturbing signals are spaced from one another by a sufficient distance to preclude significant interference therebetween.

In accordance with yet another aspect of the present invention, a method for determining the cross direction responses and mappings of actuation cells extending across the width of a machine used for manufacturing a web of sheet material comprises the steps of: applying a perturbing signal $u(k,t)$ to a k-th actuation cell during time t, the perturbing signal $u(k,t)$ alternating about a neutral state of the k-th actuation cell to minimize mean effects over any given time period of signal application; measuring a property of the web of sheet material produced by the machine during application of the perturbing signal $u(k,t)$ to generate a corresponding web property signal $y(i,t)$ where i indicates the cross direction location and t indicates the time of application; and, correlating the perturbing signal $u(k,t)$ and the web property signal $y(i,t)$ to determine the cross direction response $r(k,i)$ of the k-th actuation cell at the i-th cross direction location which also defines the mapping of the k-th actuation cell into the cross direction locations i for the property. The step of correlating the perturbing signal $u(k,t)$ and the web property signal $y(i,t)$ preferably comprises the steps of taking the covariance of $u(k,t)$ and $y(i,t+d)$ and dividing the resulting covariance with the covariance of $u(k,t)$ with itself, where d is the transportation delay between applying the perturbing signal $u(k,t)$ and measuring the web of sheet material to generate the web property signal $y(i,t)$ plus dynamic delays associated with control of the k-th actuator cell.

In accordance with still another aspect of the present invention, a system for determining the cross direction responses and mappings of actuation cells extending across the width of a machine used for manufacturing a web of sheet material comprises excitation pattern generating means for applying a perturbing signal to at least one actuation cell. The perturbing signal alternates about a neutral state of the actuation cell to minimize mean effects over any given time period of signal application. Sensor means monitor the web of sheet material and generating a profile signal representative of one or more characteristics of the web of sheet material in the machine cross direction. To determine the cross direction response and mapping of the at least one actuation cell for one or more characteristics, processor means are provided for correlating the perturbing signal and the profile signal. The amplitude of the perturbing signal is gradually increased from a low level to a level at which web characteristic perturbations resulting from the perturbing signal are distinguishable from noise perturbations encountered during normal machine operation. In this way, the system can be assured of accurately determining mappings and responses without forcing the web outside specified limits.

In accordance with an additional aspect of the present invention, a system for determining the cross direction responses and mappings of actuation cells extending across the width of a machine used for manufacturing a web of sheet material comprises excitation pattern generating means for applying perturbing signals to a plurality of the actuation cells. The perturbing signals alternate about neutral states of the actuation cells to minimize mean effects over any given time period of signal application. Sensor means monitor the web of sheet material and generate a profile signal representative of one or more characteristics of the web of sheet material in the machine cross direction. To determine the cross direction response and mapping of the plurality of actuation cells for one or more characteristics, processor means are provided for correlating the perturbing signals and the profile signal.

In accordance with yet an additional aspect of the present invention, a system for determining the cross direction responses and mappings of actuation cells extending across the width of a machine used for manufacturing a web of sheet material comprises excitation pattern generating means for applying a perturbing signal $u(k,t)$ to a k-th actuation cell during time t. The perturbing signal $u(k,t)$ is alternated about a neutral state of the k-th actuation cell to minimize mean effects over any given time period of signal application. Sensor means monitors the web of sheet material and generates a profile signal $y(i,t)$ where i indicates the cross direction location and t indicates the time, the profile signal being representative of one or more characteristics of the web of sheet material in the machine cross direction and including the effects of the perturbing signal $u(k,t)$ on the one or more characteristics. Processor means are provided for correlating the perturbing signal $u(k,t)$ and the profile signal $y(i,t)$ to determine the cross direction response $r(k,i)$ of the k-th actuation cell at the i-th cross direction location which also defines the mapping of the k-th actuation cell into the cross direction locations i for the one or more characteristics.

It is thus an object of the present invention to provide an improved method and apparatus for more rapidly and accurately determining the mappings and responses of actuation cells of web forming machines; to provide an improved method and apparatus for more rapidly and accurately determining the mappings and responses of actuation cells of web forming machines by applying perturbing signals to the actuation cells, measuring the resulting perturbation signals in the web, and correlating the perturbing signals with the perturbation signals; to provide an improved method and apparatus for more rapidly and accurately determining the mappings and responses of actuation cells of web forming machines wherein perturbing signals which alternate from a neutral position are applied to the actuation cells and are formed to minimize mean effects to the web over any given period of time such that the mappings and responses of actuation cells can be determined without interrupting or interfering with operation of the machine; and, to provide an improved method and apparatus for more rapidly and accurately determining the mappings and responses of actuation cells of web forming machines wherein perturbing signals comprising a pool of pseudo-random binary sequences are applied to the actuation cells and are correlated with resulting perturbation signals to arrive at the mappings and responses of the actuation cells.

Other objects and advantages of the invention will be apparent from the following description, the accompanying drawings and the appended claims.

BRIEF DESCRIPTION OF THE DRAWINGS

FIG. 4 is a graph of an excitation pattern usable in the present invention;

FIG. 5 is a graph of a response pattern which would result in the profile or web property signal as the result of the excitation pattern shown in FIG. 4;

FIG. 11 shows the individual response curves for the 20th and 22nd actuator cells, respectively, which are calculated in accordance with the present invention when in response to the signals of FIGS. 9 and 10; and FIG. 12 shows a solid-line response curve calculated in accordance with the present invention from individual excitation of the 20th cell with the signal of FIG. 6 and a dotted-line response curve calculated under the multiple excitations of the 20th cell and the 22nd cell with the signals of FIG. 9.

DETAILED DESCRIPTION OF THE INVENTION

Figure 1:
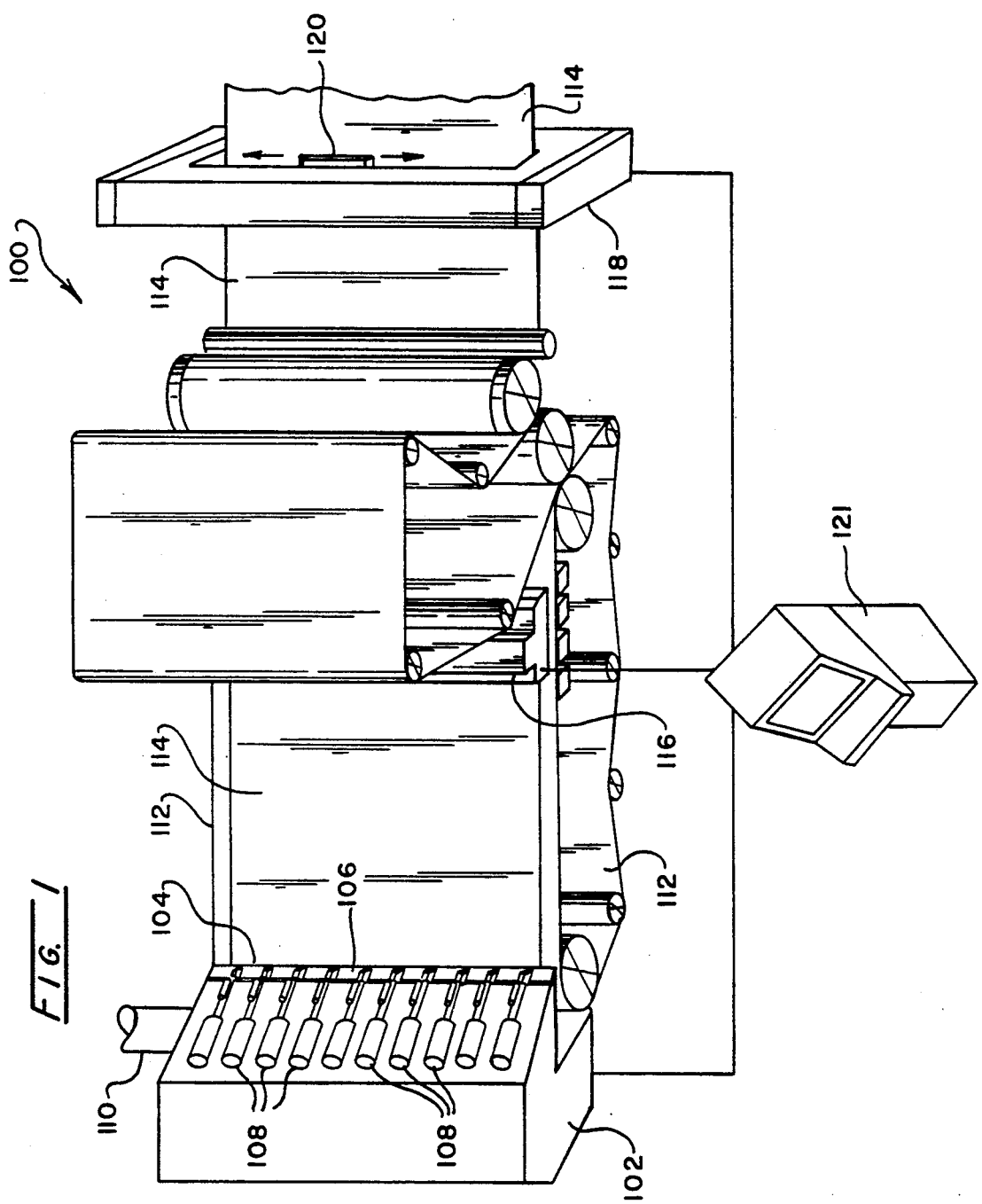
FIG. 1 is a schematic perspective plan view of a paper making machine for which the present invention is particularly applicable illustrating a headbox, a steam profiler and a web sensor platform, respectively, and also various web conveying rollers and wires.

While the present invention is generally applicable to machines for making or processing webs of sheet material, it is particularly applicable to paper making machines and accordingly will be described herein with reference to such a machine. FIG. 1 is a schematic perspective plan view of a paper making machine 100 including a headbox 102 which defines a headbox slice 104 by a slice lip 106 which is controlled along its length by actuator cells comprising basis weight actuators 108. Pulp slurry is conveyed to the headbox 102 via a stock pipe 110 such that slurry can be applied to a wire 112 to form a paper web 114. As the web 114 passes along the wire 112 and other parts of the paper making machine 100, it is processed by passing over foils, deflectors and suction boxes (not shown).

The web 114 may also be acted upon by one or more processing stations along the length of the machine 100, for example by a steam profiler 116 which includes cell actuators such as steam shower nozzles. While the present invention will be described with reference to control of the basis weight actuators 108, it is noted that it is generally applicable to the control of any form of actuator cell including steam shower nozzles, water spray IR heaters, caliper profilers and other cell actuators whether currently used or developed in the future to control a web profile of sheet material. The web 114 also passes through sensor means comprising a machine cross direction (CD) web measurement platform 118 and a sensor 120 such as a nucleonic or other appropriate sensor supported by and moved along the platform 118. The sensor 120 generates a profile signal representative of one or more characteristics of the web in the machine CD to permit control of the characteristics by processor means incorporated into an operator station 121 to thereby improve the quality of the web 114.

While a scanning sensor 120 is illustrated in FIG. 1, the present invention is equally applicable and, in fact, more advantageous if used with a sensor which simultaneously monitors the entire CD of the web 114. For example, operation of the present invention to determine the mapping and response of an entire series of actuation cells may be performed in as little as 15 minutes or possibly less where an array of CD monitors performs simultaneous monitoring.

Figure 2:
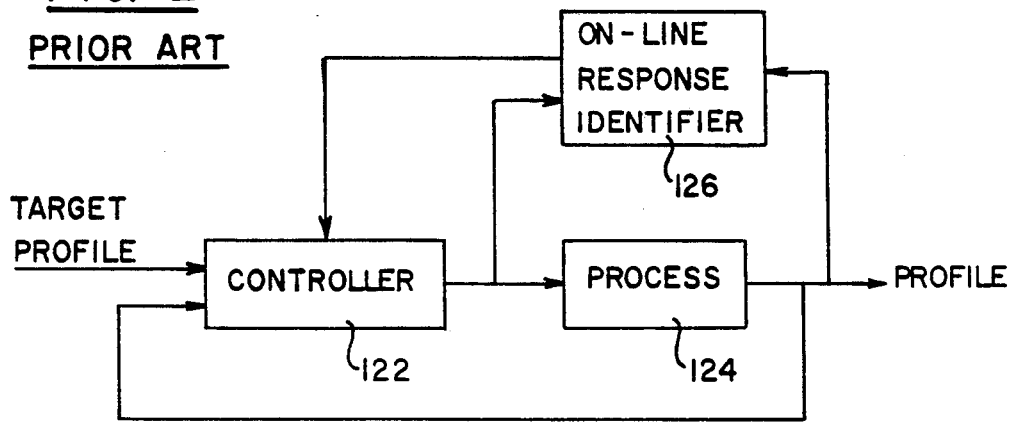
FIG. 2 is a block diagram of a prior art arrangement for identifying the mappings and responses of cell actuators from process control signals and a web profile signal.

In the past, response information has been determined on-line by means of feedback arrangements illustrated by the block diagram of FIG. 2. In these systems, process control signals are generated by a controller 122 in response to the web profile signal generated by the sensor 120 and a target signal which defines the specification limits for the web 114. The process control signals are passed to actuation cells, such as the basis weight actuators 108, of a process to be controlled represented by the process block 124. The controller 122 utilizes parameters generated by an on-line response identifier 126 in response to the process control signals from the controller 122 and the profile signal from the sensor 120.

The response identifier 126 can be operated in a known manner, for example as described in a paper entitled "Adaptive Profile Control for Sheetmaking Processes" by S.-C. Chen, R. M. Snyder and R. G. Wilhelm, Jr. which was presented at the 6th International IFAC/IFIP/IMEKO Conference on Instrumentation and Automation in the Paper, Rubber, Plastics and Polymerization Industries (PRP-6), held on Oct. 27-29, 1986 in Akron, Ohio, which paper is incorporated herein by reference. Unfortunately, since the process control signals must be substantially limited in terms of amplitude excursions, the resulting response and mapping characteristics are not as representative as is desired for optimum control of the machine 100.

An off-line system has also been described by A. Graser and W. Neddermeyer in a paper entitled "Self-Tuning Cross Profile Control For A Paper Making Machine", IFAC Application in Process Control, Istanbul, Turkey, 1986. However, operation of this system is time consuming and does not assure that the web being formed or processed is maintained within specification limits such that the web can be used.

Figure 3:
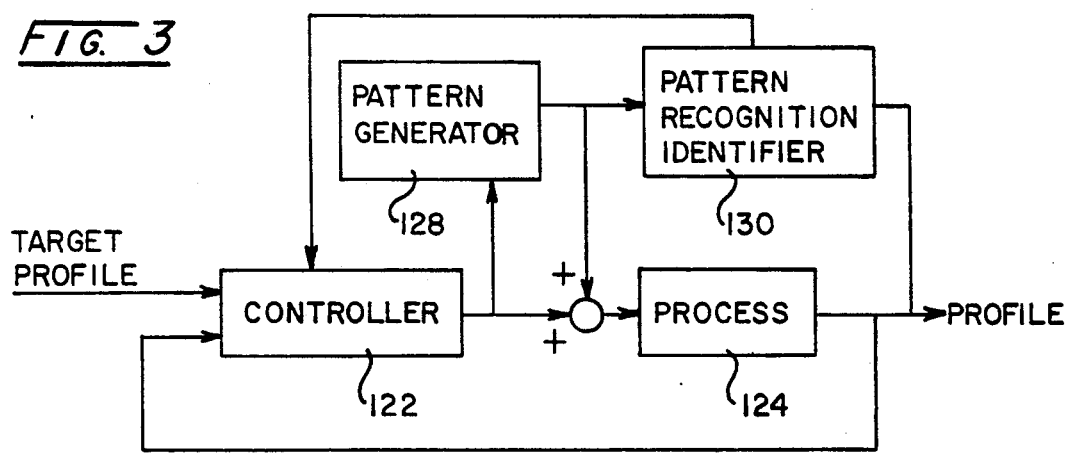
FIG. 3 is a block diagram of an arrangement for determining actuation cell mappings and responses of a web forming machine in accordance with the present invention.

Mappings and responses of actuation cells, such as the basis weight actuators 108, are relatively quickly and accurately obtained by the method and apparatus of the present invention. In the present invention, the process control signals from the controller 122 of the machine 100 are temporarily interrupted and replaced by an alternating perturbing signal generated by a pattern generator 128. The perturbing signal is applied to one, a grouping, or all of a given variety of actuation cells of the machine 100 such as the actuators 108, see FIG. 3. The effects of the alternating signal on the web appear within that area of the web which is affected by the actuation cell(s) such that the mapping and the response of the actuation cell(s) can be determined by monitoring that portion of the web which is formed while the alternating signal is applied to the actuation cell(s).

In the present invention, the mapping and/or response of each actuation cell is obtained by correlating or matching the patterns of the perturbing signal and a web property signal or profile signal obtained by monitoring the web formed by the machine 100 via the sensor 120. In the block diagram of FIG. 3, the correlation is performed by a pattern recognition identifier 130. It is noted that more than one variety of actuation cells can be probed simultaneously with the present invention provided the characteristics of the web affected by the differing actuation cells can be simultaneously monitored and do not interact with one another. Interaction of differing cell varieties could even be tolerated provided that independent signals were applied and such interaction did not cause the web characteristics to exceed specification limits.

A key element of the present invention is the excitation pattern or patterns which are generated by the pattern generator 128. In practice, correlation operations and the generation of excitation signal patterns is performed by processor means which may, for example, be incorporated into the operator station 121 of FIG. 1. It is noted that any perturbing signal applied to an actuation cell for process probing or excitation purposes should be of sufficient magnitude to generate a perturbation which can be distinguished from noise perturbations generated by normal operation of the process. However, the perturbing signal preferably is also sufficiently small that the web 114 remains within the specification limits, since otherwise the machine production during probing operations is not usable.

With this in mind, the excitation pattern should have the following properties: 1) the perturbing signal should alternate from a neutral position of the actuating cell being perturbed; 2) the perturbing signal should be selected to minimize mean effects to the characteristics of the web being probed over any given period of time; 3) at least for initial probing of a process, the amplitude of the perturbing signal should be gradually increased from a very low level if not zero until an identifiable, usable perturbation is observable in the web, an allowable mechanical limit of the actuation cell is reached, or a specified time limit for application of the perturbing signal has been exceeded; and, 4) the time duration of each movement is randomly distributed between specified limits dependent upon the actuation cell being probed, e.g. longer time durations are required for a web which is being scanned, for example 2 to 10 scans, as opposed to one which is being monitored simultaneously across its entire width.

An excitation pattern 132 which meets these criteria is shown in FIG. 4 and a corresponding response pattern 134 which would result in the profile or web property signal as the result of the excitation pattern 132 is shown in FIG. 5. The pattern alternates in the form of a pseudo-random binary sequence from the neutral position of the actuation cell which is determined at the time the excitation pattern signal is to be applied. The mean effects on the web 114 over any given period of time is limited by the alternations about the neutral position and the duration limits on each alternation. The amplitude of the alternations, starting from substantially zero, is increased until the response is sufficiently large to be distinguished from the process noise (or the mechanical or time limits are reached).

It is noted that the response pattern shown in FIG. 5 has been exaggerated for descriptive purposes since the perturbations are to be limited to levels within the specifications limits to prevent production of unusable product. Such large excitations are not required for operation of the method and apparatus of the present invention. Further, while patterns having all of the noted desired properties are preferred, several other patterns can be used if desired in given applications of the invention. For example, square waves, sine waves and regular pseudo-random binary sequences can be used in certain applications. Such alternate patterns are particularly applicable where individual actuation cells or groups of separated actuation cells are to be probed.

Figure 6:
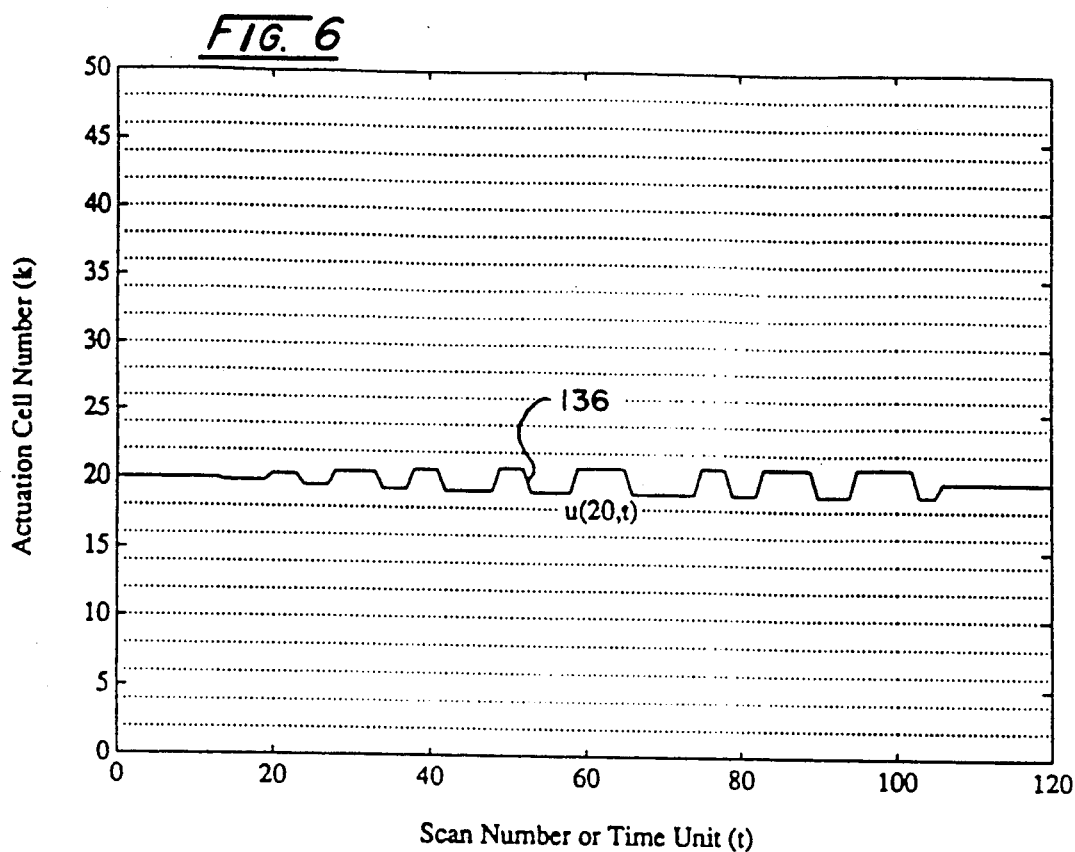
FIG. 6 shows a perturbing signal corresponding to the excitation pattern of FIG. 4 which is applied to the 20th actuation cell of a web forming machine.
Figure 7:
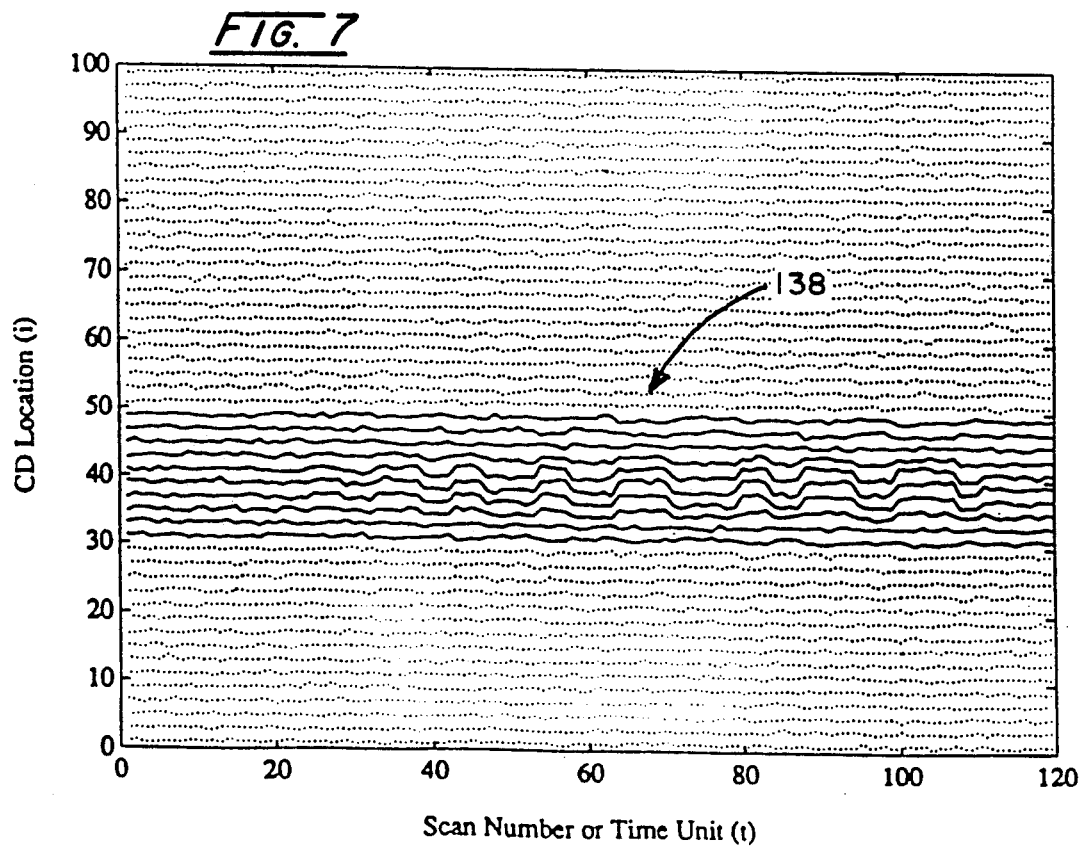
FIG. 7 shows the responses to the perturbing signal of FIG. 6.

When a perturbing signal 136 corresponding to the excitation pattern 132 shown in FIG. 4 is applied to an actuation cell, for example the 20th cell as shown in FIG. 6, the responses to the perturbing signal 136 appear within a certain area 138 of the web 114 and are recognized by the sensor 120 as shown in FIG. 7. In the area 138 of FIG. 7 where the responses can be seen, the pattern of the responses are similar to the perturbing signal 136 or excitation pattern 132. The correlation between the perturbing signal 136 and the resulting profile signals shown in FIG. 7 produces the response and mapping of the probed or excited actuation cell, i.e. the 20th cell as shown in FIG. 6. The correlation or pattern matching technique is a key feature of the present invention.

FIG. 7 illustrates the web measurements at all CD locations while the perturbing signal 136 is applied to the 20th actuation cell. The visible responses to the perturbing signal disappear beyond a certain CD distance from the center location of the primary response. The CD range that is affected by the perturbing signal 136 represents the mapping of the probed or excited actuation cell. The correlation between the perturbing signal 136 or excitation pattern 132 and the visible responses within the area 138 determines the size of the response at each CD location and the mapping of the probed or excited actuation cell. Appropriate correlation calculations for use in the present invention will now be described.

We will define $u(k,t)$ as representing the perturbing signal 136 applied to the k-th actuation cell during the time t. The two dimensional measurements of the characteristics of the web 114 performed by the sensor 120 is represented by $y(i,t)$ where i indicates the CD location and t is the "time stamp" of the measurement $y(i,t)$ and indirectly indicates the MD location of the measurement along the web 114. The correlation between $u(k,t)$ and $y(i,t)$ for all CD locations i is calculated using the formula:

$$r(k,i) = [\text{covariance or likelihood function of } u(k,t) \text{ and } y(i, t+d)]/a(k) \quad (1)$$

where
- d is the transportation delay or lag between the actuation cell and the measurement plus the dynamic delays of the actuator cell and process;
- $a(k)$ is the covariance of $u(k,t)$ with itself; and
- $r(k,i)$ is the response of the k-th actuation cell at the i-th CD location.

Formula (1) can be calculated either in batches or recursively. Recursive calculation with an adjustable forgetting factor appears to be preferable at the present time. After $r(k,i)$ is calculated for all i, a zero-phase shifting spatial filter is applied to remove the noise in the response curves $r(k,i)$. The spatial filter is defined by the following equation:

$$rf(k, i) = f_0 * r(k, i) + f_1 * [r(k, i+1) + r(k, i-1)] + f_2 * [r(k, i+2) + r(k, i-2)] + \ldots + f_s * [r(k, i+s) + r(k, i-s)]$$

where $[f_0, f_1, f_2, \ldots, f_s]$ are the coefficients of a spatial filter, for example as described in the referenced paper by Chen et al.

Figure 8:
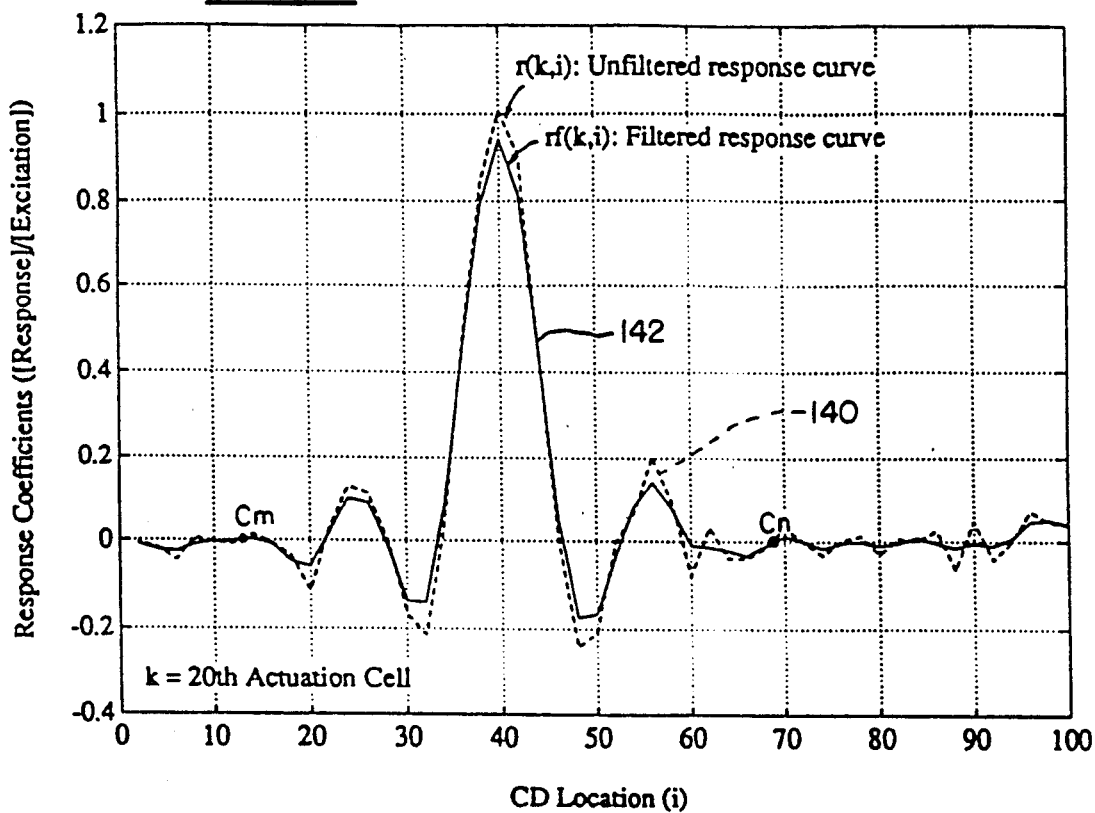
FIG. 8 shows both a filtered and unfiltered response curve for the 20th actuator cell resulting from a correlation of the perturbing signal and the responses to the perturbing signal of FIGS. 6 and 7, respectively.

For the example shown in FIGS. 6 and 7, a typical response curve 140 calculated from the correlation between $u(k,t)$ and $y(i,t)$ for all CD locations, i, is plotted in dotted lines in FIG. 8. A filtered response curve 142 is also plotted in solid lines in FIG. 8. The region which is affected by the k-th actuation cell is determined by comparing the response with the noise deadband for the process. The range from $c_m$ to $c_n$ on FIG. 8 indicates the response width of the k-th actuation cell and the scaled correlation curve between $c_m$ and $c_n$ is the response of the k-th actuation cell. The center location of the response of the k-th actuation cell, $m(k)$, is also preferably determined and such determination can be made by applying the following formula:

$$m(k) = [\text{sum}_1/\text{sum}_2] - 0.5$$

where
- $\text{sum}_1$ is the sum of $rf(k,i)*i$ for all $i = c_m$ to $c_n$; and
- $\text{sum}_2$ is the sum of $rf(k,i)$ for all $i = c_m$ to $c_n$.

A perturbing signal may be applied to a group of actuation cells across the machine which cells are spaced from one another such that there is substantially no interference between the perturbing signals. Such signals can be correlated with the resulting perturbations to determine the mappings and responses of the actuation cells which were excited or perturbed. Once the responses are determined for that group of cells, a different group of cells can be excited to determine their responses and mappings. Alternately, a piece-wise linear interpolation can be applied to estimate the response locations and response shapes for those actuation cells which have not been probed.

One of the important features of the present invention is the ability to apply multiple excitation patterns to some or all of the actuation cells, even to cells which are immediately adjacent to one another. For such multiple excitation, a pool of substantially independent excitation or perturbing patterns are created and saved. Within a continuous group of actuation cells, each pattern is unique such that it uniquely identifies the actuation cell to which it is applied. Thus, for any given continuous group of actuation cells, the unique pattern for each cell can be thought of as a "bar code" or "cell-print" for the cell. In this way, the perturbations which result from exciting a given cell within a group of continuous cells can be identified and separated from the perturbations resulting from excitation of other cells within the group.

While the group of cells does not have to be continuous for the use of a pool of substantially independent excitation or perturbing patterns, in its broadest application, the use of such a pool of patterns permits all actuation cells across a machine to be excited or probed simultaneously. Simultaneous stimulation substantially reduces the time required to generate mappings and responses for the actuation cells. For simultaneous stimulation, the actuation cells are divided into a plurality of groups of cells. The pool of excitation signals is ordered such that the patterns are applied to the groups in the same order, i.e., pattern #1, pattern #2, .... pattern #x; pattern #1, pattern #2, .... pattern #x; pattern #1, pattern #2, .... pattern #x; and so forth, until each actuation cell is assigned a unique pattern within its group. In this way, repeated patterns are spaced from one another by a sufficient distance that there is substantially no interference between or among repeated patterns.

Preferably, the pool of patterns are selected from a large number of psuedo-random binary sequences which are generated in a known manner. A binary sequence is selected to be within the pool if the sequence has a correlation with all other sequences within the pool which is less than 5%. Accordingly, all sequences within the pool are statistically independent of one another.

Figure 9:
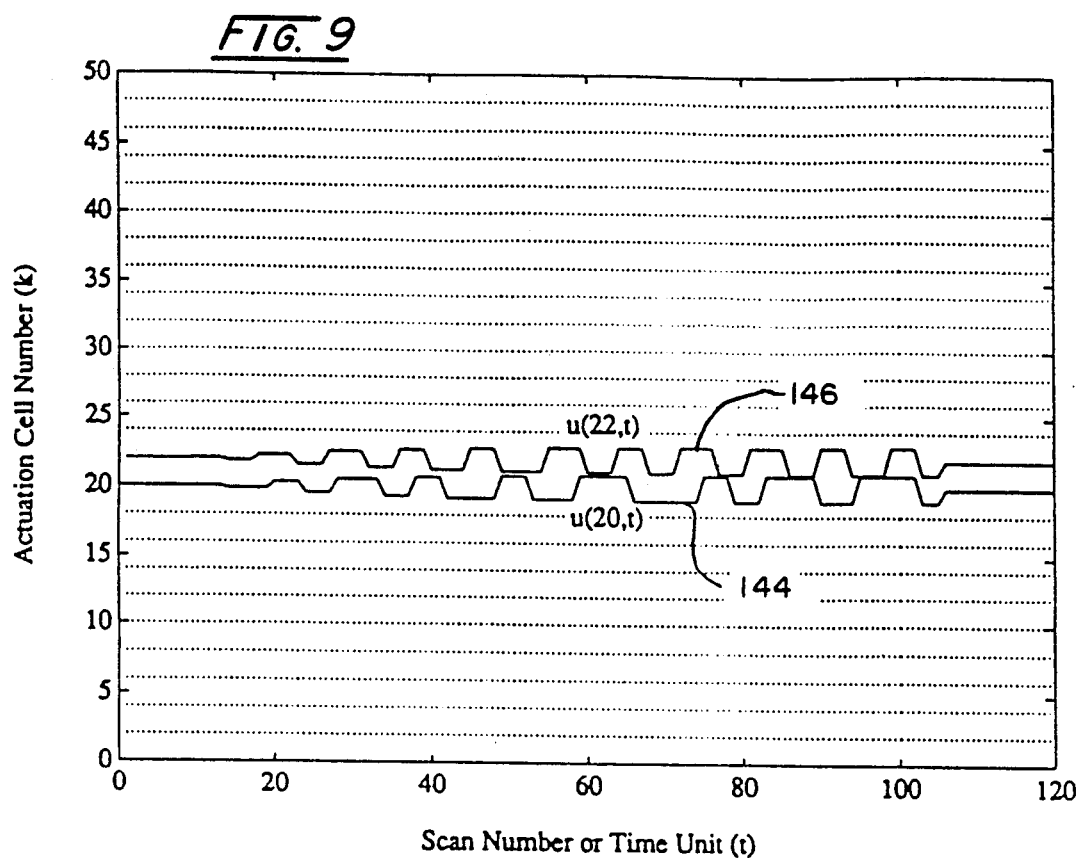
FIG. 9 shows two substantially independent excitation signals which are applied to the 20th and 22nd actuation cells of a web forming machine.
Figure 10:
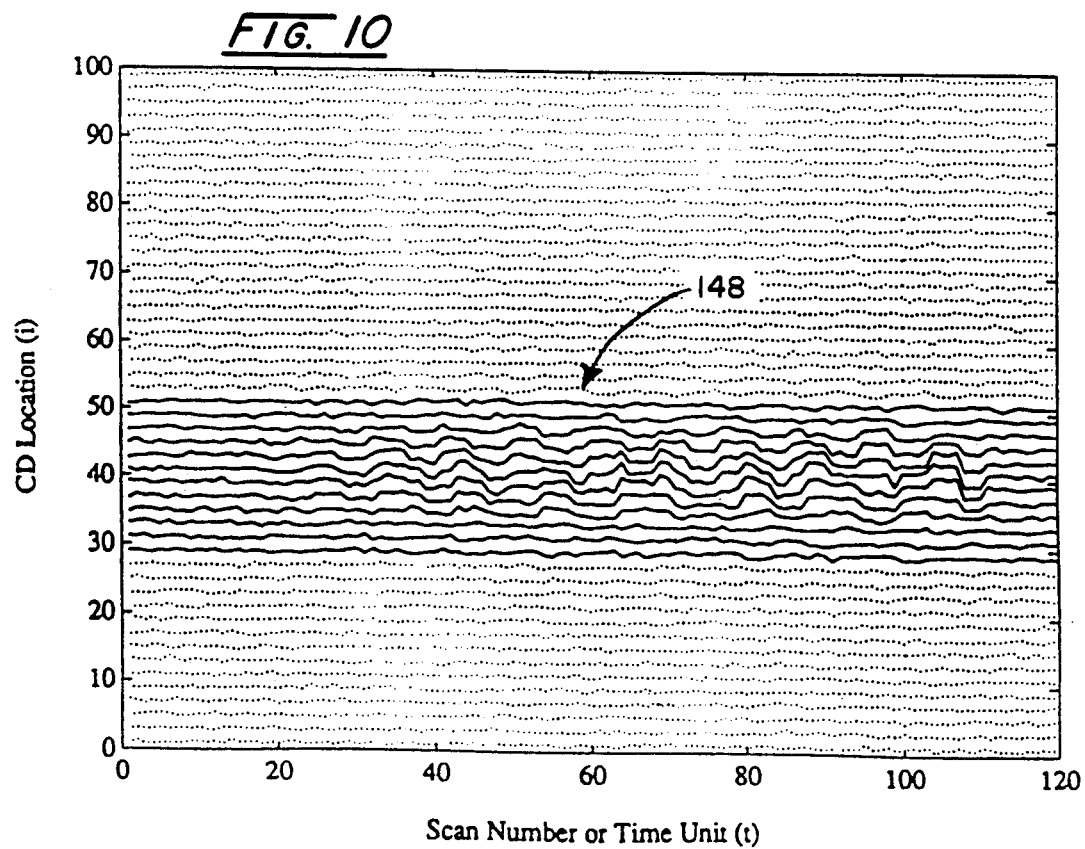
FIG. 10 shows the overlapping perturbations which result in the profile or web property signals in response to the excitation signals of FIG. 9.

When any group of actuation cells is excited or probed by a corresponding group of different patterns from the pool of substantially independent patterns, each cell is actuated with its own identifying excitation pattern. For example, two such signals 144, 146 are shown as being applied to two cells, the 20th and 22nd cells, in FIG. 9. The overlapping perturbations resulting in the area 148 of the profile or web property signals generated by the sensor 120 are shown in FIG. 10.

Although it is not easy to visualize the separate impacts of the signals 144, 146 on the resulting perturbations in the area 148, the response curves for the 20th and 22nd actuation cells can be accurately identified and distinguished by applying the correlation calculations previously defined. FIG. 11 shows the individual response curves 150, 152 for the 20th and 22nd actuators, respectively, which are calculated when the correlation calculations of the present application are applied to the signals of FIGS. 9 and 10.

To compare the accuracy of response curves which are generated from the application of individual excitation signals to the response curves which are generated by the application of multiple excitation signals, the 20th actuation cell of a machine was excited with the signal 144 alone and together with the excitation of the 22nd cell with the signal 146. FIG. 12 shows the solid-line response curve 154 calculated in accordance with the present invention from individual excitation of the 20th cell with the signal 144 and the dotted-line response curve 156 calculated with the multiple excitations of the 20th cell with the signal 144 and the 22nd cell with the signal 146. As is apparent, the response curves 154 and 156 are almost identical to one another.

Accordingly, it is possible with the present invention to probe all actuation cells simultaneously to obtain complete mapping and response information at one time. However, it may be preferred to probe the actuation cells of a machine sequentially in several groups. In each group, a set of substantially independent patterns is applied to the actuation cells. The probing operation is performed group by group until all actuation cells are probed and a complete set of response and mapping information is generated. Of course, it is also possible to probe a single actuation cell or a number of cells if a problem arises in the area serviced by the cell or number of cells, which problem is identified by variations from the web specifications.

In actual applications of the present invention, it may not be apparent what amplitude of excitation signal is sufficiently large to obtain usable perturbations in the web characteristics yet not so large that the perturbations to the web exceed acceptable specification limits. For these instances, a conservative approach is to start the perturbing signal at a very small amplitude, if not zero, and to gradually increase the amplitude of the perturbing signal as shown in FIG. 1. The amplitude of the perturbing signal is then gradually increased until the resulting perturbations in the web reach a desired signal-to-noise ratio, a maximum mechanical limit is reached for the actuation cell or cells being probed, or a time out is signaled of the probing operation.

The final amplitude is then recorded and can be used as the perturbing signal amplitude when the actuation cell or cells are to be once again probed under similar operating conditions. By storing a satisfactory amplitude for the perturbing signal, the required probing time is minimized and yet the possibilities of disruption of the product being produced by the machine are minimized. This initialization procedure can be utilized for any number of different sets of operating conditions, different product grades or other variables in a web forming or processing machine to more precisely determine initial settings for application of the present invention. By using the present invention for each product grade or distinct operating condition for a machine and developing data bases corresponding to the grades/conditions, shorter transition times are possible for grade change and machine start-up.

The present invention can be used as either a start-up procedure when a new machine is installed or as an on-line identification and correction procedure for an existing machine. When a process is running with an automatic controller for CD actuation cells, the invention can be triggered by a controlled variable, such as sheet thickness, exceeding limits defined by the specifications for the product being produced. All actuation cells can be evaluated by the present invention or only those cells which correspond to the portion of the web which has exceeded the limits. In any event, all or a portion of the automatic control is suspended temporarily while the probing operation is performed on all or that portion of the actuation cells which have caused the problem. After the response curves and mapping information have been determined, the automatic control is resumed with the updated response and mapping information.

As previously noted, the probing signal may be gradually increased until a functional amplitude is attained. It is important that the perturbing signal be stopped after satisfactory results have been obtained to prevent any further disturbance in the product being produced by the machine. The determination to stop a perturbing signal preferably should be made individually for each actuation cell.

Having thus described the method and apparatus for determining the response and mapping of actuation cells of web forming or processing machines of the present invention in detail and by reference to preferred embodiments thereof, it will be apparent that modifications and variations are possible without departing from the scope of the invention defined in the appended claims.

What is claimed is:

1. A method for determining the cross direction responses and mappings of actuation cells extending across the width of a machine used for manufacturing a web of sheet material, the method comprising the steps of:

applying a perturbing signal to at least one actuation cell, said perturbing signal alternating about a neutral state of said actuation cell to minimize mean effects over any given time period of signal application;

measuring a property of the web of sheet material produced by the machine during application of said perturbing signal to generate a corresponding web property signal; and correlating the perturbing signal and the web property signal to determine the cross direction response and mapping of said at least one actuation cell for the property.

2. A method for determining the cross direction responses and mappings of actuation cells extending across the width of a machine used for manufacturing a web of sheet material as claimed in claim 1 further comprising the step of modulating said perturbing signal such that its amplitude is gradually increased from a low level to a level at which web property perturbations resulting from said perturbing signal are distinguishable from noise perturbations encountered during normal machine operation.

3. A method for determining the cross direction responses and mappings of actuation cells extending across the width of a machine used for manufacturing a web of sheet material as claimed in claim 2 wherein the duration of alternations of said perturbing signal is randomly distributed between defined limits.

4. A method for determining the cross direction responses and mappings of actuation cells extending across the width of a machine used for manufacturing a web of sheet material as claimed in claim 1 wherein the step of applying a perturbing signal comprises applying a perturbing signal to a plurality of actuation cells which are spaced apart from one another by a distance such that perturbations generated by the application of said perturbing signal to any one of said plurality of actuation cells does not substantially affect perturbations generated by the application of said perturbing signal to any other one of said plurality of actuation cells.

5. A method for determining the cross direction responses and mappings of actuation cells extending across the width of a machine used for manufacturing a web of sheet material as claimed in claim 1 further comprising the step of determining the center of the response of said at least one actuation cell.

6. A method for determining the cross direction responses and mappings of actuation cells extending across the width of a machine used for manufacturing a web of sheet material, the method comprising the steps of:

applying perturbing signals to a plurality of said actuation cells, said perturbing signals alternating about a neutral state of said actuation cells to minimize mean effects over any given time period of signal application;

measuring a property of the web of sheet material produced by the machine during application of said perturbing signals to generate a corresponding web property signal; and correlating said perturbing signals and the web property signal to determine the cross direction responses and mappings of said plurality of actuation cells for the property.

7. A method for determining the cross direction responses and mappings of actuation cells extending across the width of a machine used for manufacturing a web of sheet material as claimed in claim 6 wherein said perturbing signals comprise a plurality of substantially independent excitation patterns.

8. A method for determining the cross direction responses and mappings of actuation cells extending across the width of a machine used for manufacturing a web of sheet material as claimed in claim 6 wherein said perturbing signals comprise a plurality of statistically independent pseudo-random binary sequences.

9. A method for determining the cross direction responses and mappings of actuation cells extending across the width of a machine used for manufacturing a web of sheet material as claimed in claim 6 wherein perturbing signals are applied to all of said actuation cells, said perturbing signals comprising a plurality of statistically independent pseudo-random binary sequences.

10. A method for determining the cross direction responses and mappings of actuation cells extending across the width of a machine used for manufacturing a web of sheet material as claimed in claim 9 wherein said perturbing signals are applied in groups of repetitively occurring statistically independent pseudo-random binary sequences, said groups being of sufficient size such that recurring perturbing signals are spaced from one another by a sufficient distance to preclude significant interference therebetween.

11. A method for determining the cross direction responses and mappings of actuation cells extending across the width of a machine used for manufacturing a web of sheet material, the method comprising the steps of:

applying a perturbing signal $u(k,t)$ to a k-th actuation cell during time t, said perturbing signal $u(k,t)$ alternating about a neutral state of said k-th actuation cell to minimize mean effects over any given time period of signal application;

measuring a property of the web of sheet material produced by the machine during application of said perturbing signal $u(k,t)$ to generate a corresponding web property signal $y(i,t)$ where i indicates the cross direction location and t indicates the time of application; and correlating said perturbing signal $u(k,t)$ and the web property signal $y(i,t)$ to determine the cross direction response $r(k,i)$ of the k-th actuation cell at the i-th cross direction location which also defines the mapping of the k-th actuation cell into the cross direction locations i for the property.

12. A method for determining the cross direction responses and mappings of actuation cells extending across the width of a machine used for manufacturing a web of sheet material as claimed in claim 11 wherein the step of correlating said perturbing signal $u(k,t)$ and the web property signal y(i,t) comprises the steps of taking the covariance of u(k,t) and y(i,t+d) and dividing the resulting covariance with the covariance of u(k,t) with itself, where d is the transportation delay between applying the perturbing signal u(k,t) and measuring the web of sheet material to generate the web property signal y(i,t) plus dynamic delays associated with control of said k-th actuator cell.

13. A system for determining the cross direction responses and mappings of actuation cells extending across the width of a machine used for manufacturing a web of sheet material, the system comprising:
excitation pattern generating means for applying a perturbing signal to at least one actuation cell, said perturbing signal alternating about a neutral state of said actuation cell to minimize mean effects over any given time period of signal application;
sensor means for monitoring the web of sheet material and generating a profile signal representative of one or more characteristics of the web of sheet material in the machine cross direction; and
processor means for correlating the perturbing signal and the profile signal to determine the cross direction response and mapping of said at least one actuation cell for one or more characteristics.

14. A system for determining the cross direction responses and mappings of actuation cells extending across the width of a machine used for manufacturing a web of sheet material as claimed in claim 13 wherein the amplitude of said perturbing signal is gradually increased from a low level to a level at which web characteristic perturbations resulting from said perturbing signal are distinguishable from noise perturbations encountered during normal machine operation.

15. A system for determining the cross direction responses and mappings of actuation cells extending across the width of a machine used for manufacturing a web of sheet material as claimed in claim 13 wherein the duration of alternations of said perturbing signal is randomly distributed between defined limits.

16. A system for determining the cross direction responses and mappings of actuation cells extending across the width of a machine used for manufacturing a web of sheet material, the system comprising:
excitation pattern generating means for applying perturbing signals to a plurality of said actuation cells, said perturbing signals alternating about a neutral state of said actuation cells to minimize mean effects over any given time period of signal application;
sensor means for monitoring the web of sheet material and generating a profile signal representative of one or more characteristics of the web of sheet material in the machine cross direction; and
processor means for correlating the perturbing signals and the profile signal to determine the cross direction response and mapping of said plurality of actuation cells for one or more characteristics.

17. A system for determining the cross direction responses and mappings of actuation cells extending across the width of a machine used for manufacturing a web of sheet material as claimed in claim 16 wherein said perturbing signals comprise a plurality of substantially independent excitation patterns.

18. A system for determining the cross direction responses and mappings of actuation cells extending across the width of a machine used for manufacturing a web of sheet material as claimed in claim 16 wherein said perturbing signals comprise a plurality of statistically independent pseudo-random binary sequences.

19. A system for determining the cross direction responses and mappings of actuation cells extending across the width of a machine used for manufacturing a web of sheet material as claimed in claim 16 wherein perturbing signals are applied to all of said actuation cells, said perturbing signals comprising a plurality of statistically independent pseudo-random binary sequences.

20. A system for determining the cross direction responses and mappings of actuation cells extending across the width of a machine used for manufacturing a web of sheet material as claimed in claim 19 wherein said perturbing signals are applied in groups of repetitively occurring statistically independent pseudo-random binary sequences, said groups being of sufficient size such that recurring perturbing signals are spaced from one another by a sufficient distance to preclude significant interference therebetween.

21. A system for determining the cross direction responses and mappings of actuation cells extending across the width of a machine used for manufacturing a web of sheet material, the system comprising:
excitation pattern generating means for applying a perturbing signal u(k,t) to a k-th actuation cell during time t, said perturbing signal u(k,t) alternating about a neutral state of said k-th actuation cell to minimize mean effects over any given time period of signal application;
sensor means for monitoring the web of sheet material and generating a profile signal y(i,t) where i indicates the cross direction location and t indicates the time, said profile signal being representative of one or more characteristics of the web of sheet material in the machine cross direction and including the effects of said perturbing signal u(k,t) on said one or more characteristics; and
processor means for correlating said perturbing signal u(k,t) and said profile signal y(i,t) to determine the cross direction response r(k,i) of the k-th actuation cell at the i-th cross direction location which also defines the mapping of the k-th actuation cell into the cross direction locations i for said one or more characteristics.

* * * * *